United States Patent
Chun et al.

(10) Patent No.: US 7,976,797 B2
(45) Date of Patent: Jul. 12, 2011

(54) ADVANCED MATERIALS FOR REGENERATIVE PYROLYSIS REACTORS, METHODS, AND REACTORS USING THE SAME

(75) Inventors: Changmin Chun, Belle Mead, NJ (US); Frank Hershkowitz, Liberty Corner, NJ (US)

(73) Assignee: ExxonMobil Chemical Patents Inc., Houston, TX (US)

(*) Notice: Subject to any disclaimer, the term of this patent is extended or adjusted under 35 U.S.C. 154(b) by 466 days.

(21) Appl. No.: 12/099,251

(22) Filed: Apr. 8, 2008

(65) Prior Publication Data
US 2009/0250377 A1 Oct. 8, 2009

(51) Int. Cl.
C10G 57/00 (2006.01)
(52) U.S. Cl. ........ 422/630; 422/631; 422/206; 208/106; 208/113; 208/133; 208/134; 208/146
(58) Field of Classification Search ........... 208/106, 208/113, 133–134, 146; 422/171, 175, 190, 422/198, 206, 208, 211–212, 220, 223
See application file for complete search history.

(56) References Cited

U.S. PATENT DOCUMENTS

| | | | |
|---|---|---|---|
| 2,319,579 A | 8/1939 | Black | |
| 2,319,679 A | 4/1942 | Hasche et al. | |
| 2,678,339 A | 5/1954 | Harris | |
| 2,692,819 A | 10/1954 | Hasche et al. | |
| 2,790,838 A | 4/1957 | Schrader | |
| 3,093,697 A | 6/1963 | Kasbohm et al. | |
| 4,360,598 A * | 11/1982 | Otagiri et al. | 501/103 |
| 5,080,872 A * | 1/1992 | Jezl et al. | 422/201 |
| 6,726,850 B1 * | 4/2004 | Reyes et al. | 252/373 |
| 2003/0105172 A1* | 6/2003 | Bowe et al. | 518/728 |
| 2004/0014826 A1* | 1/2004 | Wang et al. | 518/726 |
| 2007/0191664 A1 | 8/2007 | Hershkowitz et al. | |

FOREIGN PATENT DOCUMENTS

| | | |
|---|---|---|
| EP | 1386665 | 2/2004 |
| GB | 1 064 447 | 4/1967 |

OTHER PUBLICATIONS

Stanford Research Institute report entitled "Acetylene", a Process Economics Program, Report No. 16, Sep. 1966.
Fuel Processing Technology publication (42), entitled "Pyrolysis of Natural Gas: Chemistry and Process Concepts", by Holmen, et al., 1995, pp. 249-267.
Chemical Economy and Engineering Review, Jul./Aug. 1985, vol. 17, No. 7.8 (No. 190), pp. 47-48.
Pertti Auerkari, Mechanical and Physical Properties of Engineering Alumina Ceramics, Technical Research Centre of Finland, 1996, pp. 1-26.

* cited by examiner

*Primary Examiner* — Walter D Griffin
*Assistant Examiner* — Brian McCaig

(57) ABSTRACT

In one aspect, the invention includes an apparatus for pyrolyzing a hydrocarbon feedstock in a regenerative pyrolysis reactor system, the apparatus comprising a regenerative pyrolysis reactor comprising a stabilized refractory grade zirconia in a reactive region of the reactor system. In another aspect, this invention includes a method for pyrolyzing a hydrocarbon feedstock using a reverse flow regenerative pyrolysis reactor comprising the steps of providing a reverse flow regenerative pyrolysis reactor including a stabilized refractory grade zirconia in a heated reaction zone of the reactor; and pyrolyzing a hydrocarbon feedstock within the reactive region.

25 Claims, 3 Drawing Sheets

Illustrative examples of normalized thermal shock resistance (NTSR) ranked from 1 to 5:

ADVANCED MATERIALS FOR REGENERATIVE PYROLYSIS REACTORS, METHODS, AND REACTORS USING THE SAME

FIELD OF THE INVENTION

This invention pertains to materials, methods, and apparatus useful in regenerative pyrolysis reactors such as may be used for thermally converting hydrocarbons. The invention relates to materials, apparatus, and methods for cracking hydrocarbon feedstocks in a high-severity, regenerative pyrolysis reactor. More particularly, the invention relates to reactor materials that facilitate improved process reliability and equipment durability.

BACKGROUND OF THE INVENTION

Conventional steam crackers are an effective tool for cracking high-quality feedstocks that contain a large fraction of volatile hydrocarbons, such as ethane, propane, naphtha, and gas oil. Similarly, regenerative pyrolysis reactors, including reverse flow pyrolysis reactors ("RFR"), are also used for converting or cracking hydrocarbons and to execute cyclic, high temperature chemistry such as those reactions that may be performed at temperatures higher than can suitably be performed in conventional steam crackers.

Acetylene (or ethyne, HC≡CH) has long been recognized as one of the few compounds that can be made directly at high selectivity from methane pyrolysis but the conditions of that manufacture have placed it beyond commercial practicality for other than high cost, specialty production. Acetylene can be converted to a number of other desirable hydrocarbon products, such as olefins and vinyls. One of the biggest impediments to producing acetylene from methane or other hydrocarbon feeds has been the very high temperatures required to produce high-yield conversion of methane to acetylene. Many of the desired products that could be manufactured from the produced acetylene are today instead being produced via more economical processes, such as thermal cracking of higher molecular weight hydrocarbon feeds such as ethane, propane, naphthas, and gas-oil, in steam crackers. The higher molecular weight feeds generally crack at lower temperatures than methane. Equipment, materials, and processes were not previously identified that could continuously withstand the high (>1500° C.) temperatures required for methane pyrolysis. Pyrolyzing large quantities of methane into acetylene for conversion to olefins had been considered too costly and impractical due to the special types and costs of equipment that would be required. The developed commercial processes for producing acetylene have all operated at lower temperatures (e.g., <1500° C.) and are generally related to steam cracking of higher weight hydrocarbon feeds.

It is known that acetylene may be manufactured from methane in relatively small amounts or batches, using high temperature and short contact time in cyclical processes, yielding a mixture of acetylene, CO, and $H_2$. Comprehensive discussions are provided in the Stanford Research Institute report entitled "Acetylene," a Process Economics Program, Report No. 16, September 1966, and in the Fuel Processing Technology publication (42), entitled "Pyrolysis of Natural Gas: Chemistry and Process Concepts," by Holmen, et. al., 1995, pgs 249-267. However the known processes are inefficient compared to commercial steam cracking, do not scale well, and are generally only useful for specialty applications.

Regenerative reactors, including reactors such as disclosed by Wulff (discussed below), are typically used to execute cyclic, batch-generation, high temperature chemistry. Regenerative reactor cycles typically are either symmetric (same chemistry or reaction in both directions) or asymmetric (chemistry or reaction changes with step in cycle). Symmetric cycles are typically used for relatively mild exothermic chemistry, examples being regenerative thermal oxidation ("RTO") and autothermal reforming ("ATR"). Asymmetric cycles are typically used to execute endothermic chemistry, and the desired endothermic chemistry is paired with a different chemistry that is exothermic (typically combustion) to provide heat of reaction for the endothermic reaction. Examples of asymmetric cycles are Wulff cracking, pressure swing reforming ("PSR"), and other regenerative pyrolysis reactor processes.

The known art discloses that to efficiently obtain relatively high yields of acetylene from methane feed, such as in excess of 50 wt. %, preferably in excess of 75 wt. % acetylene from the methane feed, temperatures are required to be in excess of 1500° C. and preferably in excess of 1600° C., with short contact times (generally <0.1 seconds, with rapid quenching) to prevent decomposing the acetylene into coke and hydrogen. Such temperature and processes have largely been unattractive due to thermal, chemical, and mechanical degradation of the equipment utilized. Virtually any metal components directly exposed to such temperatures and stress due to cyclical temperature fluctuations, will be costly and unacceptably degrade over time. Although regenerative pyrolysis reactors are generally known in the art as capable of converting or cracking hydrocarbons, they have not achieved commercial or widespread use, due at least in part to the fact that they have not been successfully scaled well to a commercially economical size or commercially useful life span. These drawbacks to wide scale commercialization are due in large part to the inability of the equipment to adequately control and contend with the very high temperatures.

A related challenge has been in controlling how fuel and oxidant are combined during the regeneration or heating stage of the process. Inability to effectively control this issue contributes to the degradation of components and inefficiency at commercial scale. Due to uncontrolled exothermic reaction, the created high temperatures are difficult to position and contain for extended periods of time and lead to premature equipment failure.

Another challenge relates to materials stability at high temperature. Many prior art reactor materials undergo or become susceptible to chemistry alterations at the high process temperatures. The alterations lead to premature equipment degradation and potentially even interference with the process chemistry.

Complicating the issue still further for regenerative or cyclic reverse flow reactors has been the detrimental effects upon materials that are exposed to the large, cyclic temperature swings encountered during the process. Such effects become even more pronounced for high severity pyrolysis processes. A solution was proposed in a U.S. patent application filed Dec. 21, 2006, Ser. No. 11/643,541, entitled "Methane Conversion to Higher Hydrocarbons," related primarily to methane feedstocks for pyrolysis systems, utilizing an inventive deferred combustion process. Although the disclosed process effectively controls the location of combustion, the internal reactor components must still contend with the severely high temperatures incurred in methane or other hydrocarbon pyrolysis for a commercially acceptable duration.

Typically, regenerative reactors include a reactor bed or zone comprising some type of refractory material in the reactive regions of the reactor, including the regions where the pyrolysis conversion or cracking reaction takes place and possibly also in those portions of the reactor that convey the reactants into and/or from the region where the reaction occurs. The refractory material comprising such reactive region may be a ceramic or other refractory material. Conventional regenerative reactors commonly deliver a stream of fuel, oxidant, or a supplemental amount of one of the reactants, directly to a location somewhere within the flow path of the reactor bed. In a deferred combustion regenerative reactor, the reactants are delivered separately into the region where they can mix and react at that location. The delivered reactants then are caused or permitted to exothermically react therein and heat the reactor media or bed in the reactive region of the reactor. Thereafter, direction of flow may be reversed or continue in the same direction, and the reacted components are exhausted and a pyrolysis feedstock, such as a hydrocarbon feed stream, preferably a vaporized feed, is introduced into the heated region of the media or bed. The pyrolysis feedstock is thus exposed to the heated media to cause heating and pyrolysis conversion of the reactor feedstock into a pyrolyzed reactor feed or product. The pyrolyzed reactor feed or product is then conveyed or otherwise removed from the reactive region of the reactor and quenched or cooled, such as in a quench region of the reactor system, to halt the pyrolysis reaction and yield a desired pyrolysis product, such as acetylene or ethylene.

Economics or feed availability may favor using lower cost feedstocks as feedstocks for regenerative pyrolysis reactors. As with steam crackers, regenerative pyrolysis reactors also are well suited for volatized or volatizable hydrocarbon feedstocks such as, by way of non-limiting examples, crude oil, heavy distillate cuts, contaminated naphthas and condensates, and atmospheric resids that are substantially free of nonvolatile components. Nonvolatile components, such as metals and other residual or substantially nonvolatizable components tend to "lay down" and build up in the reactor as ash, metals, and coke. Unfortunately, these economically favored feedstocks typically contain undesirable amounts of nonvolatile components and have heretofore been unacceptable as regenerative reactor feedstocks. Regenerative pyrolysis reactors do not have the flexibility to process such otherwise economically crack favorable feedstocks because, although coke can typically be burned off, deposits or buildup of ash and metals within the reactor cannot easily be burned or removed. A solution was proposed in a U.S. patent application filed Jun. 4, 2007, entitled "Pyrolysis Reactor Conversion of Hydrocarbon Feedstocks into Higher Value Hydrocarbons," disclosing an inventive reverse flow regenerative reactor system suitable for pyrolyzing feedstocks heavier than methane, particularly those feedstocks that may contain or comprise non-volatizable components.

Chemical Economy and Engineering Review, July/August 1985, Vol. 17, No. 7.8 (No. 190), pp. 47-48, discloses that furnaces have been developed commercially for steam cracking a wide range of liquid hydrocarbon feedstocks using process reaction times in the range of 0.05 to 0.1 second. This publication indicates that the use of these furnaces permits substantial increases in the yield of olefins (i.e., ethylene, propylene, butadiene) while decreasing production of less-desirable co-products. GB 1064447 describes a process for production of acetylene from pyrolysis of methane and hydrogen (e.g., 1:1 to 39:1 $H_2:CH_4$) in an electrically heated reactor and quenching with a dry, oxygen-free gas stream. The maximum temperature is 1450° C. to 2000° C. (preferably 1450° C. to 1750° C.).

The "Wulff" process represents one of the more preferred commercial processes for generation of acetylene. The Wulff process includes a reverse-flow thermal pyrolysis process and began development in the 1920's. Various related processes operated commercially up to about the 1960s. These processes typically used feeds heavier than methane and thereby operated at temperatures of less than 1500° C. The most complete description of the Wulff process is provided in the Stanford Research Institute's "Acetylene", Process Economics Program Report Number 16 (1966). Among the relevant patents listed in this report are U.S. Pat. Nos. 2,319,679; 2,678,339; 2,692,819; and 3,093,697, discussed above. It is believed that all commercial acetylene plants operated on feeds of ethane, naphtha, and/or butane, but that none have successfully operated on methane feeds. Wulff discloses a cyclic, regenerative furnace, preferably including stacks of Hasche tiles (see U.S. Pat. No. 2,319,679) as the heat exchange medium. However, to contain the location of the reaction heat generated by the exothermic combustion process, one of either the fuel or oxygen is introduced laterally or separately into the central core of the reactor where it mixes with the other reaction component therein. The other reaction component is preferably introduced through the reactor tiles to cool the reactor quench section. Thereby, combustion can occur in a targeted location within the reactor. However, the lateral introduction also exposes the lateral injection nozzles or ports to the combustion product, including the extremely high temperature needed to crack methane feeds. Degradation in nozzle performance, shape, and/or size consequently made it extremely difficult to control flame shape, temperature, and efficiency. Although some of the Wulff art disclose use of various refractory materials, a commercially useful process for methane cracking was not achieved utilizing such materials. Also, a further and more significant drawback of the Wulff process is that the laterally or separately introduced portion of exothermic reactant is not utilized for quenching the recuperation reactor bed. This imbalance in heat created and heat removed typically results in an expanding heat gradient through the reactor bed and corresponding changes in reaction timing, duration, and control. This situation creates significant difficulty with quenching the reaction at precisely the right time to produce the desired acetylene or other reaction product.

As discussed above, the technology of high-severity pyrolysis can result in high selectivity to acetylene that enables many dimensions of chemicals growth from natural gas and other hydrocarbon feeds. Analysis of the capabilities of reverse-flow reactors (RFR's) suggests that these reactors may achieve the desired reaction conditions only at extreme temperatures ($\geqq 1500°$ C. and in some cases even >1700° C.) in a cost effective manner. The aforementioned practical obstacles have impeded large scale implementation of the technologies. Materials availability for such high temperature is one of the most critical issues in design and operation of large-scale, commercial, high-productivity, RFR's.

Due to ultrahigh temperatures involved in RFR's, only ceramic components have the potential to meet the materials characteristics needed in such an aggressive application. The American Society for Testing and Materials (ASTM) defines a ceramic article as "an article having a glazed or unglazed body of crystalline or partly crystalline structure, or of glass, which body is produced from essentially inorganic, non-metallic substances and either is formed from a molten mass which solidifies on cooling, or is formed and simultaneously or subsequently matured by the action of the heat." Ceramics components generally can be categorized in three material categories: engineering grade, insulation grade, and refractory grade.

The term "engineering grade" has been applied to ceramic materials which typically have very low porosity, high density, relatively high thermal conductivity, and comprise a complete component or a lining. Examples include dense forms of aluminum oxide ($Al_2O_3$), silicon nitride ($Si_3N_4$), silicon carbide (SiC), silicon aluminum oxynitride (SIALON), zirconium oxide ($ZrO_2$), transformation-toughened zirconia (TTZ), transformation-toughened alumina (TTA), and aluminum nitride (AlN). These materials usually possess high strength and toughness, which have been dramatically improved to the degree that ceramics are now available that can compete with metals in applications previously thought impossible for ceramics. Strength is a measurement of the resistance to formation of a crack or structural damage in the material when a load is applied. Toughness is a measurement of the resistance of the material to propagation of a crack or extension of damage to the point of failure. For instance, engineering grade $Al_2O_3$ and SiC are commercially available with a strength of over 345 MPa, and $Si_3N_4$ and TTZ are available with strengths above 690 MPa (100 kpsi). Some TTZ materials have toughness around 15 MPa·$m^{1/2}$, which is an order of magnitude higher than that of conventional ceramics. Even though engineering grade ceramics have superior strength and toughness at relatively low temperatures, they are relatively poor in thermal shock resistance and many grades, such as but not limited to borides, carbides, and nitrides are not chemically stable at high temperature. Many are also not suitable for use at the high temperatures encountered with some pyrolysis reactions.

The second category of ceramic materials is insulation grade ceramics, which are typified by relatively high porosity. Many may have fibrous crystalline grain structures and are more porous than engineering grade ceramics, have lower density, and have lower thermal conductivity than engineering grade ceramics. Insulating monolithic ceramics and composite ceramics are often fabricated into various forms such as rigid boards, cylinders, papers, felts, textiles, blankets, and moldables. Many are primarily used for thermal insulation at elevated temperatures, such as up to 1700° C. A broad range of porosities and pore sizes can be produced, depending on the intended application, but in general, insulation grade ceramics tend to be relatively porous as compared to engineering grade ceramics. Porous ceramics have many open or closed internal pores that provide the thermal barrier properties. Often, porous ceramics, such as having porosity of for example, greater than 50 vol. % and commonly even in excess of 90 vol. %, are used for thermal insulation where extremely low thermal conductivity (<0.08 W/m·K) is required. However, insulation grade ceramics usually lack the structural strength and functional toughness needed for the internal components of RFR's that are directly exposed to the pyrolysis reactions and flowing, hot reactants or products. Insulation grade ceramics typically are recognized as having a flexural strength or toughness of less than about 4 Kpsi (27.6 MPa) and often of less than even 1 Kpsi (6.9 MPa). Also, the insulation properties of porous ceramics may also tend to degrade over time as the relatively large pores may tend to fill with coke accumulation.

The third general category of ceramic materials is refractory grade ceramics. Many refractory grade ceramics typically have porosity, strength, and toughness properties that tend to be intermediate to these properties in engineering grade and insulation grade. Refractory grade ceramics typically have higher thermal shock resistance properties and maximum use temperatures than most insulation grade and engineering grade ceramics. However, refractory grade ceramics have other properties that may vary as compared to engineering and insulation grade ceramics that distinguish each of the various refractory grade ceramics from the engineering and insulation grade ceramics, and from each other. Each of these other properties must also be considered when selecting a refractory grade ceramic for a particular application. Some of the other relevant properties or characteristics include but are not limited to maximum use temperature, thermal conductivity, modulus of rupture, modulus of elasticity, electrical resistance, average grit size, density, porosity, and purity. The maximum use temperature is the highest temperature to which refractory ceramics can be exposed without degradation. Thermal conductivity is the linear heat transfer per unit area for a given applied temperature gradient. The modulus of rupture (MOR) or cross-break strength is the maximum flexural strength that refractory ceramics can withstand before failure or fracture occurs. Young's modulus or the modulus of elasticity is a material constant that indicates the variation of strain produced under an applied tensile load. Average grit size measures the size of individual grains or crystals within the microstructure of a polycrystalline ceramic material. Density is the mass per unit of bulk volume. Purity is the percentage, by weight, of major constituents.

As compared to insulation grade ceramics, refractory grade ceramics tend to be stronger across broader temperature ranges. Refractory grade ceramics also generally tend to be more resistant to thermal shock than insulation or engineering grade ceramics. However, while some refractory grade ceramics tend to be somewhat inert or chemically stable at elevated temperatures, some refractory grade ceramics become chemically and/or structurally unstable at elevated temperatures, rendering them unsuitable for applications exposed to chemical reactions. Exemplary chemically and/or thermally unstable ceramics include certain silicas, borides, carbides, and nitrides. Also, some refractory grade ceramics are also known to possess lower thermal conductivities and coefficients of expansion than certain other refractory or engineering grade ceramics. Others have variations of these properties. Refractory grade ceramics are also known to undergo alterations in crystalline structure at elevated temperatures. Such alterations can result in changes in bulk volume which can result in production of stress fractures and/or cleavage planes which can reduce the material's strength. Some exemplary, common high temperature refractory grade materials include but are not limited to magnesia (MgO), lime (CaO), and zirconia ($ZrO_2$). However, the studied art does not teach preferred crystalline structure or composition for particular reactor furnace uses.

The reviewed art is also void of teaching how to prepare or select a material having a range of properties that are suitable for use in constructing a furnace for performing substantially continuous, cyclical, high temperature pyrolysis chemistry. Also, materials testing methods commonly applied to metals and polymers are frequently less useful for testing ceramics. The available tests provide only a limited picture of the total performance limits of any particular ceramic. Further complicating the ceramic material selection process is the complexing fact that, like metals and polymers, the performance of a ceramic is also a function of temperature, with dependent changes in properties such as brittleness, elastic, plastic and viscoplastic deformation, hardness, fatigue, corrosion resistance, and creep resistance. Other important performance factors include but are not limited to thermal shock resistance, thermal expansion, elastic modulus, thermal conductivity, strength, and fracture toughness.

The identified prior art pertaining to refractory materials for high-severity hydrocarbon pyrolysis dates primarily to the 1960's and earlier. However, that art merely occasionally provides generalized lists of some exemplary materials such as ceramics, alumina, silicon carbide, and zircon as reactor materials. These sparse, non-specific disclosures left the art largely incapable of providing a large-scale, commercially useful reactor or reactor process. The teachings of the art was only effective for enabling relatively small scale specialty applications that see vastly inferior use as compared to large scale processes such as hydrocarbon steam cracking. The identified art is void of teaching or providing a refractory ceramic material that has the complex set of properties that are required for extended use in the reactive or other most-demanding regions of a high-severity ($\geqq 1500°$ C.) pyrolysis reactor for the commercial production of acetylene and/or olefins. The art needs a refractory material that can endure prolonged exposure to high severity temperatures, substantial temperature swing cycles, cyclic flows of combustion and reaction materials, and concurrently provide the needed structural integrity, crystalline stability, relatively high heat transfer capability, and chemical inertness in the presence of high temperature chemical reactions that is required for large scale, high productivity applications. Lack of materials availability and selection criteria for identifying the materials for use in the reactive and most severe temperature regions of a reactor system is one of the most critical remaining issues in design and large-scale operation of such reactors.

SUMMARY OF THE INVENTION

The present invention relates to thermal pyrolysis of hydrocarbons and in one embodiment includes an apparatus for pyrolyzing a hydrocarbon feedstock in a regenerative pyrolysis reactor system, preferably in a reverse flow regenerative pyrolysis reactor system, utilizing stabilized refractory grade zirconia ("SRZ") in a reactive region of the reactor. The SRZ may be either a fully stabilized refractory grade zirconia ("FSRZ") or more preferably a partially stabilized refractory grade zirconia ("PSRZ"). The term stabilized zirconia includes both fully stabilized zirconia and partially stabilized zirconia. SRZ and PSRZ are discussed in more detail below. For purposes herein, it is also intended that the relevant stabilized zirconias (including but not necessarily limited to the preferred zirconia having the general chemical formula $ZrO_2$) are refractory grade stabilized zirconias, such that the term "stabilized zirconia" may be synonymous with the terms "stabilized refractory grade zirconia."

In some embodiments, the SRZ comprises a monolith having flow channels therein for conducting or transmitting at least one of a pyrolysis reactant and a pyrolysis product through the monolith. The term "monolith" as used herein shall be defined broadly, including but not limited to an apparatus or conductive media typically having multiple substantially parallel flow channels through the apparatus for conducting a fluid, such as a gas, along such channels (e.g., a ceramic honeycomb such as commonly used for catalyst support, heat exchange, or in a catalytic converter).

Preferably, the SRZ includes a thermal shock resistance rating that demonstrates a total crack length per unit area after quenching a test specimen of said stabilized refractory grade zirconia at 1100° C. into a water bath at ambient or room temperature (e.g., about 50° C.) that is not greater than 30 µm/cm$^2$.

It is also preferred that the SRZ comprises a modulus of rupture (MOR) mechanical flexural strength of not less than 2 kpsi (13.8 MPa) prior to firing the SRZ-laden reactor or otherwise initially heating the SRZ material to a temperature of at least 1000° C. More preferably, it is preferred that the SRZ comprises a MOR mechanical flexural strength of not less than 2 kpsi (13.8 MPa) when the reactor is fired or otherwise heated to a temperature in a range of from 1000° C. to 1800° C. Still more preferably, it may be preferred that the SRZ comprises a MOR mechanical flexural strength of not less than 2 kpsi (13.8 MPa) when the reactor is fired or otherwise heated to a temperature in a range of from 1000° C. to 2000° C.

Many preferred apparatus according to the present invention may also include an SRZ that comprises an MOR mechanical flexural strength measured at 50° C. after water bath quenching from a temperature in a range of from 1000° C. to 1800° C. that is at least 70% of said stabilized refractory grade zirconia's MOR flexural strength measured at a temperature in a range of from 1000° C. to 1800° C. The procedure used is as described in ASTM C 1525-4. Still more preferred embodiment may include an SRZ that comprises an MOR mechanical flexural strength measured at 50° C. after water-bath quenching from a temperature in a range of from 1000° C. to 1800° C. that is at least 80% of said stabilized refractory grade zirconia's MOR flexural strength measured at a temperature in a range of from 1000° C. to 1800° C.

In most preferred embodiments, the SRZ is stabilized by at least one stabilization component that includes at least one of CaO, MgO, $Y_2O_3$, $CeO_2$, and mixtures thereof. Preferably, the SRZ comprises at least one weight percent of the stabilization component, based upon the total weight of said stabilized refractory grade zirconia. In other embodiments, the SRZ further comprises one or more secondary oxides selected from the group consisting of Al, Si, Mg, Ca, Y Fe, Mn, Ni, Co, Cr, Ti, Hf, V, Nb, Ta, Mo, W, Sc, La, and Ce, and mixtures thereof. Secondary oxides may be merely incidentally present or may be purposefully added such as to improve certain properties or uses, e.g., such as processability during manufacture. In many preferred embodiments, the SRZ is a partially stabilized zirconia (PSRZ). Preferred PSRZ, including PSRZ, may include a thermal shock resistance rating that demonstrates a total crack length per unit area after quenching a test specimen of said stabilized refractory grade zirconia at 1100° C. into a water bath at room temperature that is not greater than 5 µm/cm$^2$. Preferably, the partially stabilized refractory grade zirconia comprises a modulus of rupture (MOR) mechanical flexural strength of not less than 4 kpsi (27.6 MPa) when heated to a temperature in a range of from 1000° C. to 1800° C. It is also preferred that the PSRZ comprises a MOR mechanical flexural strength measured at 50° C. after quenching from a temperature in a range of from 1000° C. to 1800° C. that is at least 80% of said PSRZ's MOR flexural strength measured at a temperature in a range of from 1000° C. to 1800° C.

In most preferred embodiments, the stabilized refractory grade zirconia is stabilized by at least one stabilization component that includes at least one of CaO, MgO, $Y_2O_3$, $CeO_2$, and mixtures thereof. Preferably, the SRZ comprises at least one weight percent of the stabilization component, based upon the total weight of said stabilized refractory grade zirconia. In other embodiments, the SRZ further comprises one or more secondary oxides selected from the group consisting of Al, Si, Mg, Ca, Y Fe, Mn, Ni, Co, Cr, Ti, Hf, V, Nb, Ta, Mo, W, Sc, La, and Ce, and mixtures thereof.

In another aspect, the invention includes a reverse flow regenerative pyrolysis reactor system comprising a first reactor and a second reactor in flow communication with the first reactor, the first reactor comprising a first channel for conveying a first reactant through the first reactor to the second reactor and a second channel for conveying a second reactant through the first reactor to the second reactor, the first reactant exothermically reacting with the second reactant, in or proximate to the second reactor, wherein the second reactor comprises a SRZ, more preferably the SRZ is a PSRZ. Preferably, at least the first reactor comprises SRZ, and more preferably both reactors comprise the SRZ, particularly in the portions of the reactor bed that are subjected to the extremely high temperatures or to the extremely high temperature swings experienced during the cyclic reactor operation. In some preferred embodiments, the reactor system further comprises a reactant mixer intermediate the first and second reactors for combining or mixing at least a portion of the first reactant with at least a portion of the second reactant, wherein the reactant mixer comprises SRZ, and more preferably PSRZ. The mixer may be either a component that is separate from the first and/or second reactors or may be an integral portion or component of either or both of the first or second reactor that is proximate the other of the first or second reactor.

In still another aspect, the invention includes a method for pyrolyzing a hydrocarbon feedstock using a regenerative pyrolysis reactor, preferably a reverse flow regenerative pyrolysis reactor, comprising the steps of providing a regenerative pyrolysis reactor including a stabilized refractory grade zirconia, more preferably a PSRZ, in a reactive region or heated reaction zone of the reactor, and pyrolyzing a hydrocarbon feedstock within the heated reaction zone. Preferably, the method further comprises the step of heating the heated reaction zone by a deferred combustion process. In some preferred embodiments, the method includes use of a reactant mixer in or near the reaction zone, such as between the first and second reactors, for combining or mixing at least a portion of the first reactant with at least a portion of the second reactant, wherein the reactant mixer comprises PSRZ.

DETAILED DESCRIPTION

Figure 1A:
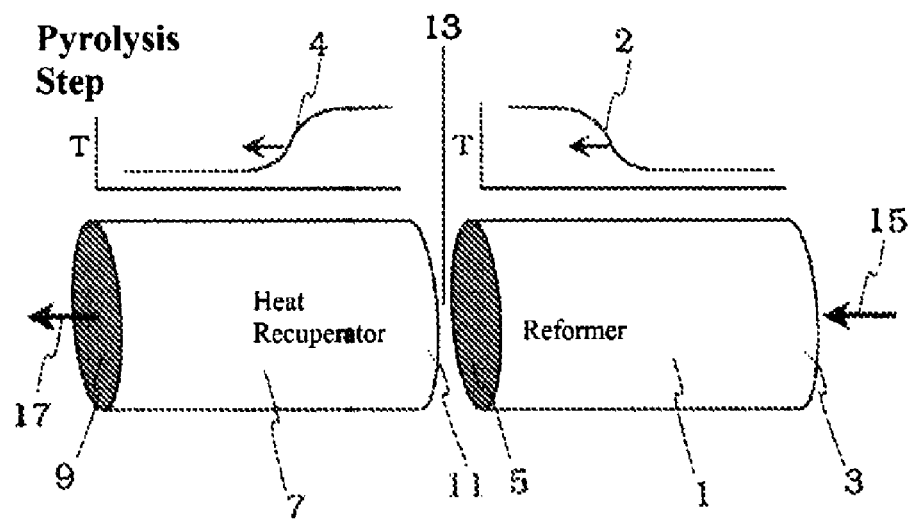
FIGS. 1(a) and 1(b) are a simplified, diagrammatic illustration of the two primary process steps in a regenerating reverse flow pyrolysis reactor system, according to the present invention.

Zirconia is a crystalline material that undergoes a change at different temperatures in the way its atoms are stacked (polymorphic transformation). Zirconia has a monoclinic crystal structure between room temperature and about 950° C. Above about 950° C., zirconia converts to the tetragonal crystal structure. This transformation is accompanied by greater than one percent volumetric shrinkage during heating and equivalent expansion during cooling. At a still higher temperature, the zirconia changes from tetragonal to a cubic structure. These volumetric changes associated with alterations in crystalline structure can produce crystalline fractures or cleavages along grain boundaries. In pure polycrystalline zirconia, this tetragonal-monoclinic transition results in a reduction in strength and potential catastrophic failure of the component.

Chemical addition of at least one mole percent of one or more of $CaO$, $MgO$, $Y_2O_3$, $CeO_2$ or mixtures thereof to the zirconia, based upon the total weight of zirconia and such additive, result in formation of a cubic crystal structure that is more crystalline-stable over the complete temperature range and does not undergo a phase transformation. Such zirconia, including at least one mole percent of one or more of $CaO$, $MgO$, $Y_2O_3$, $CeO_2$ or mixtures thereof added to the zirconia, based upon the total weight of zirconia and such additive shall be referred to in this specification and the claims appended hereto as "stabilized zirconia." $CaO$, $MgO$, $Y_2O_3$, $CeO_2$ or mixtures thereof added into the zirconia are referred to herein as "stabilizers." A stabilized zirconia may thereby include at least one mole percent of stabilizer, in other embodiments at least two mole percent of stabilizer, and in other embodiments a stabilized zirconia may include at least four mole percent of such stabilizer. For example, addition of about 16-27 mole percent $CaO$ into $ZrO_2$ generally fully stabilizes the zirconia and makes the structure cubic over the relevant, broad temperature range. Other stabilizers require varying percentages of stabilizer to fully stabilize a zirconia. For further example, about 7 mole percent of $Y_2O_3$ into the $ZrO_2$ provides a cubic crystalline structure that is stable over the relevant temperature range, such as up to 2260° C. As a still further example, the critical concentration of $MgO$ is about 12 mole percent. In yet another example, a stabilized zirconia may include a fraction of a percent of at least one of such stabilizer and another fraction of a percent of another of such stabilizer, such that the combined fractions make up at least one mole percent of the total weight of the zirconia and such additive.

Zirconia containing sufficient stabilizer to render complete or substantially complete crystallization shift to cubic structure or a zirconia having an excessive amount of stabilizer is considered a fully stabilized zirconia ("FSZ"). In contrast, addition of less stabilizer than the amount required to create a fully cubic-crystalline Zirconia structure renders the zirconia structure a mixture of cubic and monoclinic phases and/or cubic and tetragonal crystal phases. Zirconia containing such limited amount of stabilizer additive such that there remains at least more than an incidental amount of monoclinic and/or tetragonal crystals, is referred to as "partially stabilized zirconia" ("PSZ"). The term partially stabilized zirconia is thus defined to include substantially any stabilized zirconia that has at least one mole percent of stabilizer but insufficient amount of stabilizer to render a fully cubic-crystalline zirconia over the relevant, broad temperature range.

The exact division between fully and partially stabilized can be a relative term, as depicted in phase diagrams of the mixed components as a function of temperature, and is sometimes difficult to precisely discern due to factors such as incomplete stabilizer dispersion or mixing, or the presence of other non-stabilizing contaminants. For purposes of this invention, it may be considered that as the percentage of stabilizer increases from roughly none present toward an increasing stabilizer presence and corresponding increased stabilization toward full stabilization, the key strength and toughness properties generally tend to improve through the partial stabilization range. However, at some point approaching substantially complete cubic crystallization or full stabilization, these important strength and toughness properties may tend to degrade somewhat across a broad temperature spectrum as compared to such properties in a partially stabilized zirconia that has a mixture of cubic, monoclinic, and/or tetragonal crystals. However, depending upon the application, the fully or more-fully stabilized zirconia may still be useful for the intended application, while for many other applications the generally still tougher and more fracture-resistant partially stabilized zirconia will be preferable. In addition to degree of stabilization, the stabilized zirconia's performance properties may also be affected to varying degrees by other factors, such as particle sizing, particle arrangement, density, processing additives, and other properties and factors.

The detailed compositional ranges of FSZ and PSZ in given chemical additions of CaO, MgO, $Y_2O_3$ or $CeO_2$ to the $ZrO_2$ are known to a skilled artisan in the ceramics field and provided in the American Ceramic Society monograph entitled "Phase Diagrams for Ceramists," by Levin et. al. For substantially all stabilizer-zirconia compositions, it is generally appreciated that fully stabilized zirconia has relatively low fracture toughness and relatively poor resistance to impact as compared to partially stabilized zirconia, such that for many applications PSZ may be preferable to FSZ. By adding less CaO, MgO, $Y_2O_3$ or $CeO_2$ or other stabilizer to the zirconia compound than the amount of stabilizer required to completely stabilize all of the zirconia (e.g., the ZrO2) crystals, and also preferably by careful control of particle sizing, distribution, and processing, mixtures of the stabilized cubic phase and the unstable monoclinic phase that have very high fracture toughness are achieved. This type of material is referred to herein as a PSRZ.

Two key materials properties have been identified that most critically impact high-severity performance of ceramics in RFR's and their corresponding acceptability for large scale application; namely, thermal shock resistance and mechanical flexural strength. Thermal shock resistance of a ceramic component can be defined as the maximum change in temperature that the material can withstand without failure or excessive damage. Thermal shock resistance is an evaluated parameter but is not a material property. Thermal shock resistance depends upon the type of thermal cycle, component geometry, and strength as well as on material properties or factors.

Simplified mathematical expressions relying upon a variety of assumptions can be used to describe material performance under a set of conditions. Alternatively, much more complex analyses may be performed using numerical analysis methods such as finite element and stress-strain analysis. However, for materials performance comparison purposes a qualitative or direct comparative analysis is also useful. Thermal shock resistance may be evaluated by means of rapid water quench experiments such as illustrated in ASTM C1525. Thermal shock damage results in a material from buildup of thermal and physical stresses, usually during rapid heating or rapid cooling. The major materials factors influencing thermal shock resistance are thermal expansion coefficient ($\alpha$), elastic modulus (E), thermal conductivity (k), strength ($\sigma_f$), and fracture toughness ($K_{1C}$). Thermal shock resistance is increased by decreasing $\alpha$ and E and by increasing k, $\sigma_f$ and $K_{1C}$.

For example, the ASTM C1525 thermal shock resistance test method builds on the experimental principle of rapid quenching of a test specimen (e.g., 1"×1"×⅛" square, or 2.54 cm×2.54 cm×0.32 cm square) from an elevated temperature (e.g. 1100° C.) into a water bath at room temperature. After water quenching, the specimen is dried and dye-penetrated to investigate both open and closed cracks. For instance, Zyglo® water washable dye penetrants may be used. As the zirconia samples are typically white or yellow, pink dye provides a vivid depiction of cracks and helps differentiate cracks from background or grain boundaries. The electronic scanner resolution or magnification is generally not critical, e.g., from as low as from 50× to as high as 1000×. The tester need only be able to differentiate actual cracks from mere grain boundaries. The cumulative or total crack length per unit area in each specimen is determined by the scanning software aggregating the lengths of all cracks, backed up with visual confirmation by the technician. As with any specified parameter, the value determined must be made over a large enough region to provide a statistically sound representation of the entire sample. The total crack length per unit area may be determined over a sufficiently large area or by aggregating and averaging a number of smaller regions that collectively represent a statistically sound region.

Depending on propensity of cracks observed in a test specimen, the thermal shock resistance may be normalized and qualitatively ranked, such as from 1 (the least resistance) to 5 (the most resistance) as summarized hereunder:
  1: Open cracks and many closed cracks.
  2: Many closed cracks.
  3: Some closed cracks.
  4: Little closed cracks.
  5: No cracks.

Figure 3:
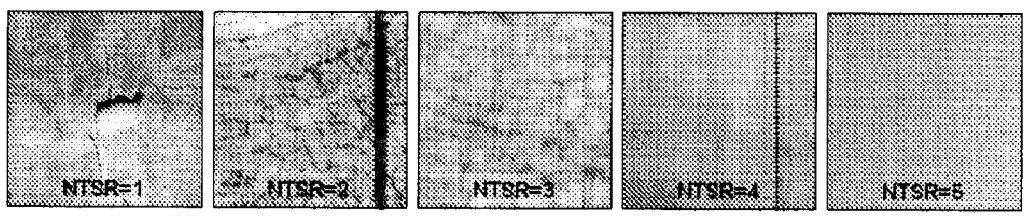
FIG. 3 provides photographic examples of stress cracking of various ceramic samples graded from 1 to 5 to illustrate corresponding normalized thermal shock resistance.

The appearance of cracks in rapidly quenched zirconia specimens and their normalized thermal shock resistance (NTSR) as ranked from 1 to 5 are illustrated in FIG. 3. A rating of 1 is least acceptable while a rating of 5 is most acceptable. To better quantify propensity of cracks observed in a thermal shock resistance test specimen, dye penetrated samples were optically scanned and subjected to an image analysis computer software program. For example, a total crack length per unit area of the test specimen may be measured by use of commercially available image analysis software, e.g., Clemex Vision PE, as reported in Table 1. Other image analysis software applications can also empower to easily measure the total crack length of the specimen.

TABLE 1

Illustrative examples of normalized thermal shock resistance (NTSR) index or rating, ranked from 1 to 5.

| NTSR Index | Measured total crack length per unit area ($cm/cm^2$) | Criteria of total crack length ($cm/cm^2$) |
|---|---|---|
| 1 | 81.2 | >50 |
| 2 | 25.6 | >30-≦50 |
| 3 | 16.5 | >5-≦30 |
| 4 | 3.5 | >1-≦5 |
| 5 | 0.01 | ≦1 |

The stabilized refractory grade zirconia of this invention includes a thermal shock resistance rating that demonstrates a total crack length per unit area after quenching a test specimen of said stabilized refractory grade zirconia at 1100° C. into a water bath at room temperature is preferably not greater than 30 $cm/cm^2$, e.g., has a NTSR of 3, 4, or most preferably 5. Preferably, the stabilized refractory grade zirconia of this invention includes a thermal shock resistance rating that demonstrates a total crack length per unit area after quenching a test specimen of said stabilized refractory grade zirconia at 1100° C. into a water bath at room temperature is preferably not greater than 5 $cm/cm^2$. Still more preferably, the stabilized refractory grade zirconia of this invention includes a thermal shock resistance rating that demonstrates a total crack length per unit area after quenching a test specimen of said stabilized refractory grade zirconia at 1100° C. into a water bath at room temperature is preferably not greater than 1 $cm/cm^2$. Therefore, a NTSR of at least 4 may be acceptable, while an NTSR rating of 5 is likely most preferred, according to the present invention. An NTSR rating of less than 4 may generally be presumed not acceptable for many desired applications.

As set forth in ASTM C 1525-04, the effect of the thermal shock can be assessed by measuring the reduction in MOR flexural strength produced by rapid quenching of test specimens heated across a range of temperatures. For purposes of this invention, regarding quantitative measurement of thermal shock resistance, a critical temperature interval may be determined by a reduction in the mean flexural strength of at least 30% for a SRZ material. However, the test does not determine thermal stresses developed as a result of a steady state temperature differences within a ceramic body or of thermal expansion mismatch between joined bodies. Further, unless the test is repeated several times, the test is not intended to quantitatively determine the resistance of a ceramic material to repeated or cyclic shocks. Thus, it is preferred that the test be repeated to analyze the effect of cyclic temperature shocks.

Flexural strength (Modulus of Rupture, MOR) can be measured by 3-point bending tests as illustrated in ASTM F417. The test specimen, a small bar of square cross section, rests on two cylindrical supports in a compression test machine. It is bent by the application of force, at mid-span, to the opposite face of the bar from that resting on the two supports. The bending force is applied by a third cylinder (identical to the other two) at a prescribed constant rate until the specimen breaks. The breaking rod, the dimensions of the specimen, and the test span are used to calculate flexural strength.

The present invention includes a pyrolysis reactor wherein the refractory grade stabilized zirconia, preferably a PSZ but may also be a FSZ, is used for construction of the key components of the reactor's reactive region. The reactive region includes but is not necessarily limited to those reactor components that are within the region of the reactor that is used to convey the reactants, intermix the reactants, define the immediate flow-path for the reactants, store and release reaction heat that enables and is consumed in the pyrolysis reaction. For purposes of the claimed invention, the reactive region includes at least a high temperature or heat-handling portion of the reactor and typically may include those components that are associated with the flow and interaction of the heat generating reactants into and within the reactor, mixing and combustion of the reactants, storage and release of the produced heat for consumption in facilitating the pyrolysis reaction, movement of the pyrolysis feed and generated products through and from within the reactor, and with quenching the reaction products. The claimed reactive region does not, however, include those conventional reactor refractory or pyrolysis components whose primary function is merely to isolate, insulate, or otherwise merely confine the generated heat, or which merely provide mechanical support for those regions of the reactor that are directly involved in or proximate to the reaction heat. The reactive region does not include reactor components that are merely peripheral to the flowing media or which are only incidentally heated, such as reactor peripheral insulation, even though a stabilized refractory grade zirconia may find application in such uses. The reactive region is defined more by function than by component name and for purposes of this invention includes those portions of the reactor which function to directly contact the flowing media or reactants, reaction heat, provide conveyance of the reactants, thereby performing a heat-handling or product conveying function pertaining to the pyrolysis reaction, rather than merely playing a passive heat confining, refractory or structural role. The term reactive region also includes those reactor components that are subject to cyclic, wide temperature swings, and in the case of a reverse flow reactor includes those regions that are also exposed to alterations in the direction of media flow in addition to the cyclic temperature swings. By way of example and not as a limitation, the reactive region may include reactor components such as conductive monoliths, thin-walled honeycombs, bead-beds, mixers, quench media, and other reactor components, regardless of whether simple or complex shaped, that are directly associated with the pyrolysis reaction. According to the invention, the reactive region includes those components or internals within the pyrolysis reactor system that are directly exposed to the high temperature reactions and also generally to the heated products. Such components are preferably fabricated from the claimed stabilized zirconia.

In some preferred embodiments, in addition to the amount of stabilizer present, the microstructure of the stabilized refractory grade zirconia may also includes an optimum level of porosity (say for example, 10-30 vol. % porosity). The porosity may also contribute to the stabilized zirconia's performance and help impart superior physical and mechanical properties and thermal shock performance.

Figure 4:
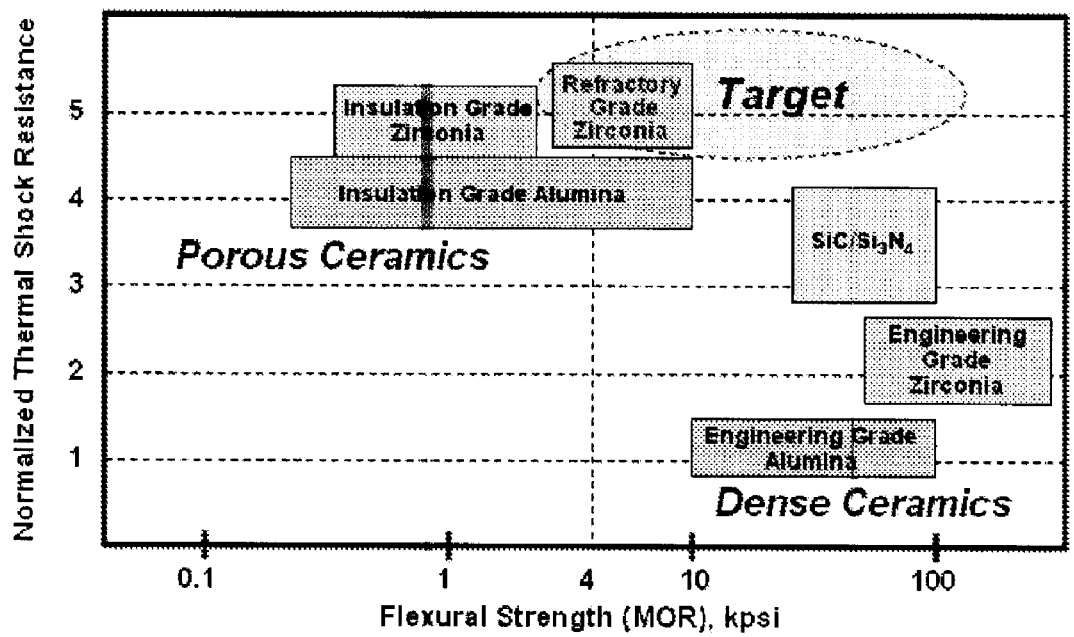
FIG. 4 provides a generalized illustration of typical ranges of normalized thermal shock resistance vs. flexural strength of various ceramic materials.

Although the most preferred stabilized zirconia embodiments may benefit from consideration of a multitude of properties in determining the commercial fitness of a particular zirconia material, the relationship of the two key properties of the preferred refractory grade stabilized zirconia are most essential. Examples of these two properties are illustrated below in FIG. 4. FIG. 4 generally compares the relationship of the two performance properties for various families of ceramics, including the targeted area for a preferred ceramic material according to this invention. It is preferred that normalized thermal shock resistance of the refractory grade zirconia must be at least about 3 times better than a standard engineering grade alumina (e.g., $\geq 80$ wt % $Al_2O_3$) and more preferably at least about 4 times better. Thermal shock tested standard engineering grade alumina reveals open cracks and many closed cracks, when subjected to the temperatures of most interest. Thus, by definition, the normalized thermal shock resistance (NTSR) of engineering grade alumina may also be assigned a quantitative thermal shock resistance rating performance value of 1. The thermal shock resistance of the stabilized refractory grade zirconia of this invention has a thermal shock resistance rating of at least 3, preferably 4, and even more preferably 5. An NTSR rating of 4 or more preferably even 5 will be required for many applications of most commercial interest.

As a ceramic material is heated, its density typically increases as a result of pore shrinkage due to the sintering effect caused by the heat, as compared to the density at ambient temperature prior to such heating. Sintering may result in some of the ceramic crystals or components therein melting or undergoing other high temperature fusion or shrinkage, resulting in a slight decrease in bulk volume. Thus, as a ceramic is heated, its modulus of rupture mechanical flexural strength (MOR) may typically also correspondingly increase slightly. However, when the hot ceramic is subjected to relatively quick cooling, such as via water quenching, stress fractures may be introduced thereby causing a weakening or reduction in the mechanical flexural strength. There are at least two determinations of mechanical flexural strength (MOR) that are of key interest in determining the suitability of a particular ceramic with regard to the present invention. One is the MOR that is measured at high or operating temperature, (e.g., such as from 1000° C. to 1800° C.), which is typically greater than or equal to the MOR measured after cooling by quenching. The other MOR of interest is the retained MOR that is measured at room temperature after quenching. The relevant determination of interest then is the percent retained strength at room or ambient temperature, after quenching. ASTM 1505 describes such a process for such determination.

The MOR of the preferred SRZ used for reactor components according to this invention must be greater than or equal to about 2 kpsi (13.8 MPa) after initial heating to operating temperature. Preferably, the MOR must also be greater than or equal to about 2 kpsi (13.8 MPa) after subsequent quick quenching to room temperature. Also, the MOR is greater than or equal to about 2 kpsi (13.8) when the reheated sample is measured at operating temperature range such as from 1000° C. to 1800° C. or even more preferably from 1000° C. to 2000° C. About 2 kpsi (13.8 MPa) is recognized herein as a minimal MOR strength across the required broad reactor temperature spectrum that is necessary to provide minimum mechanical integrity in the relevant reactor components. A commercially sized reactor will typically have such SRZ components stacked or positioned within the reactor core and must retain mechanical integrity to accommodate such structuring. More preferably, the initial, high temperature MOR should be greater than or equal to about 4 kpsi (27.6 MPa) and even more preferably greater than or equal to about 10 kpsi (69 MPa). To put in perspective the technology challenge, these materials performance targets are compared with selected engineering grade and insulation grade ceramics. For instance, some of engineering grade alumina or zirconia ceramics may provide superior flexural strength, but their thermal shock resistance is poor. Some advanced engineering ceramics, such as SiC and $Si_3N_4$, also provide superior strength, but their thermal shock resistance in grossly inadequate. Moreover, these silicon based ceramics can not be used at high temperatures (i.e. >1500° C.) due to high temperature oxidation issue. On the other end of the spectrum lie the insulation grade ceramics. These ceramics offer excellent thermal shock resistance, but they fall quite short of the required strength performance.

With regard to the other MOR determination, e.g., that of retained strength after quenching, preferred apparatus according to the present invention also include an SRZ that comprises an MOR mechanical flexural strength measured at 50° C. after water bath quenching from a temperature in a range of from 1000° C. to 1800° C. that is at least 70% of said stabilized refractory grade zirconia's MOR flexural strength measured at a temperature in a range of from 1000° C. to 1800° C. As stated previously, the minimum MOR strength must also be at least 2 kpsi (13.8 MPa) to maintain the structural integrity of the ceramic structure. Still more preferred embodiments may include an SRZ that comprises an MOR mechanical flexural strength measured at 50° C. after water-bath quenching from a temperature in a range of from 1000° C. to 1800° C. that is at least 75% of said stabilized refractory grade zirconia's MOR flexural strength measured at a temperature in a range of from 1000° C. to 1800° C. In still more preferred embodiments, the SRZ is a partially stabilized refractory grade ceramic and the partially stabilized refractory grade zirconia includes an MOR mechanical flexural strength measured at 50° C. after water-bath quenching from a temperature in a range of from 1000° C. to 1800° C. that is at least 80% of said partially stabilized refractory grade zirconia's MOR flexural strength measured at a temperature in a range of from 1000° C. to 1800° C.

FIG. 4 illustrates generally, some performance properties of various families or types of ceramics. FIG. 4 compares the properties of thermal shock resistance versus MOR. However, as illustrated in FIG. 4, the performance target for these two properties of the preferred or targeted ceramic generally extends to and encompasses the upper reaches or limits of both of these properties for ceramics. It is a feature of this invention that use of a stabilized zirconia and more preferably use of a partially stabilized zirconia, having thermal shock resistance and MOR properties as indicated in FIG. 4 may facilitate large scale commercial operation of a high severity pyrolysis reactor.

The preferred ceramic is a high performing refractory grade zirconia and more particularly, a high performing stabilized refractory grade zirconia (SRZ), and still more preferably, a partially stabilized refractory grade zirconia (PSRZ), prepared in a manner to provide operation such as illustrated generally in or near the preferred target zone of FIG. 4. Surprisingly, a properly prepared, stabilized zirconia ceramic, most particularly a partially stabilized zirconia, provides properties not found in any of the widely known ceramic families, including those commonly used for refractory applications. These two properties are most critical to regenerative reactor success at extreme temperatures. Surprisingly, the desired performance range of these two properties in the material used in a high severity regenerative reactor extend beyond the performance limits of the commonly used types of engineering grade ceramics, insulation grade ceramics, and even many refractory grade ceramics, and are most determinative of the long-term success of such operation. Although not included in FIG. 4, the data ranges illustrated are also a function of the degree of stabilization that is performed to the ceramic.

Table 2 illustrates the thermal shock resistance and flexural strength of selected commercial engineering grade, insulation grade, and refractory grade ceramic materials that were tested under the conditions as described above, according to the procedure described in ASTM 1525.

TABLE 3

| Grade | Ceramics | Manufacturer (™) | Trade Name (™) | Normalized Thermal Shock Resistance | Flexural Strength (kpsi/MPa) |
| --- | --- | --- | --- | --- | --- |
| Engineering | Alumina | CoorsTek | AD-998 | 1 | 54/373 |
| | $Y_2O_3$-PSZ | CoorsTek | YZTP | 2 | 250/1725 |
| | MgO-PSZ | CoorsTek | TTZ-A4 | 1 | 78/538 |
| | ZTA | CoorsTek | ZTA | 1 | 65/449 |
| | SiC | Saint-Gobain | Hexoloy ® SA | 4 | 65/449 |
| | $Si_3N_4$ | Ceradyne | EKasin ® 2000 | 3 | 60/414 |
| Insulation | $Y_2O_3$-FSZ | Zircar Zirconia | FBD | 5 | 1.2/8.3 |
| | Alumina | Zircar Zirconia | BusterM-45 | 4 | 1.3/9.0 |
| Refractory | Alumina | North American Refractory Co. | Tufline ® 98 DM | 3 | 2.8/19.3 |

TABLE 3-continued

| Grade | Ceramics | Manufacturer (™) | Trade Name (™) | Normalized Thermal Shock Resistance | Flexural Strength (kpsi/MPa) |
|---|---|---|---|---|---|
| | MgO-PSZ | Zircoa | Comp.3077 | 5 | 5.0/34.5 |
| | CaO-PSZ | Zircoa | Comp.1661 | 5 | 4.8/33 |

Flexural strength of the refractory grade MgO-PSRZ was measured after heating test specimens at various temperatures. Zircoa's™ composition 3077 refractory was used for the experiment and is exemplary of a PSRZ that may be suitable for use in a pyrolysis reactor, according to the invention. The composition 3077 is a MgO partially stabilized zirconia (2.6 wt. % MgO) coarse grain, sintered body having density about 4.9 g/cc and porosity of about 14 vol. %. It contains about 62% monoclinic phase. In addition to MgO, it contains some chemical impurities including about 1.2 wt. % $SiO_2$, 0.1 wt. % $Al_2O_3$, 0.1 wt. % CaO, 0.4 wt. % $Fe_2O_3$ and 0.2 wt. % $TiO_2$.

Figure 5:
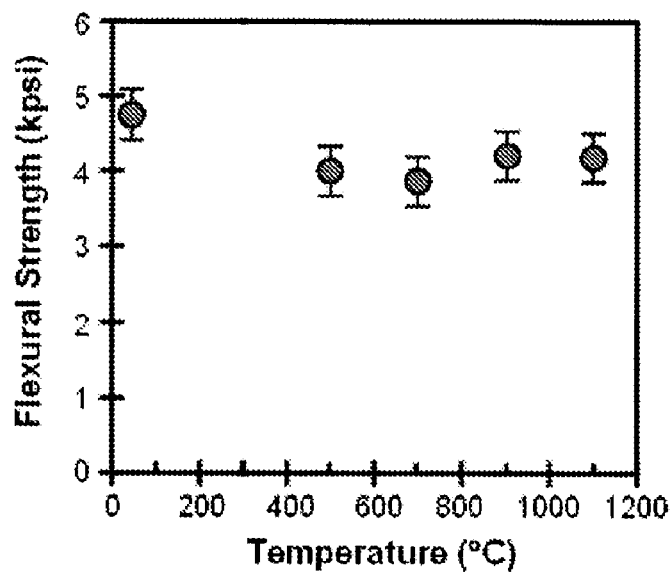
FIG. 5 provides a generalized illustration of flexural strength vs. temperature for the refractory grade specimen.

FIG. 5 illustrates, for example, flexural strength versus temperature that the each MgO-PSRZ specimen was heated to before water quenching. Data suggests flexural strength was almost retained after severe thermal shock, revealing only about up to 20% reduction in flexural strength as compared to flexural strength at ambient temperature. Since there was no abrupt change in the flexural strength, this material may be rated as having superior thermal shock resistance.

In one aspect, this invention includes a regenerative pyrolysis reactor apparatus for pyrolyzing a hydrocarbon feedstock, the apparatus including a regenerative pyrolysis reactor comprising a stabilized refractory grade zirconia (SRZ) in a reactive region of the reactor. Preferably, the regenerative pyrolysis reactor comprises a reverse flow type of regenerative pyrolysis reactor. In another preferred embodiment, the reactive region includes at least one of flow channels, (such as but not limited to a honeycomb monolith or other media conductor), or a reaction bed, (such as but not limited to, another honeycomb monolith, a reactor bead bed, mixer). In another embodiment, the apparatus further comprises refractory grade insulation material in a substantially non-reactive region of the reactor, that is, in a region other than the reactive region. Such refractory grade insulation may be a SRZ or any other suitable refractory material. The SRZ is used in at least those regions of the reactor that are exposed to the intense heat. (e.g., $\geq 1500°$ C.). Preferably the SRZ comprises all of the reactor components within the hot regions.

The term hydrocarbon feedstock may be defined broadly to include virtually any hydrocarbonaceous feed. Exemplary hydrocarbon pyrolysis feedstocks that may have particular applicability for use in the present invention typically comprises one or more hydrocarbons such as methane, ethane, propane, butane, naphthas, gas oils, condensates, kerosene, heating oil, diesel, hydrocrackate, Fischer-Tropsch liquids, distillate, heavy gas oil, steam cracked gas oil and residues, crude oil, crude oil fractions, atmospheric pipestill bottoms, vacuum pipestill streams including bottoms, heavy non-virgin hydrocarbon streams from refineries, vacuum gas oils, low sulfur waxy residue, heavy waxes, atmospheric residue, and heavy residue and hydrocarbon feeds. Solids and non-volatiles contained in the feedstreams may be removed by one or more separation techniques, prior to feeding a volatizable fraction into the reactor. Unless otherwise stated, all percentages, parts, ratios, etc. are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed.

This invention includes but is not limited to use of apparatus and methods disclosed in various, previous patent applications, the entirety of each of which are included herein by reference, including (i) U.S. application Ser. No. 60/753,961, filed Dec. 23, 2005, titled "Controlled Combustion for Regenerative Reactors," (ii) U.S. application Ser. No. 11/639, 691, filed Dec. 15, 2006, titled "Controlled Combustion for Regenerative Reactors;" (iii) U.S. application Ser. No. 11/643,541, filed Dec. 21, 2006, titled "Methane Conversion to Higher Hydrocarbons;" and (iv) U.S. provisional patent application Ser. No. 60/933,044, filed Jun. 4, 2007, titled "Pyrolysis Reactor Conversion of Hydrocarbon Feedstocks Into Higher Value Hydrocarbons." These patent applications teach and disclose various apparatus and methods for pyrolyzing hydrocarbon feeds in reverse flow regenerative pyrolysis reactors, including deferred combustion and controlled heat positioning processes. The inventions disclosed in this present invention may be suitable for use with but not limited to reactors as disclosed in these previous applications. In preferred embodiments, the inventive reverse flow regenerative pyrolysis reactor system utilizes deferred combustion in a reverse flow reactor to heat the SRZ.

The term "pyrolysis" as used herein may be defined to include the use of heat or thermal energy, whether produced directly, such as by furnace, or indirectly such as by exothermic reaction, combustion, or heat transfer from a heated media, to cause the molecular conversion, reforming, degrading, or cracking of a hydrocarbon feedstock into a product stream, and may optionally include supplementation by one or more of catalysis, hydrogenation, diluents, and/or stripping agents.

At least part of the invention of the present inventors is an apparatus and process providing that the requisite high heat may be achieved by creating a high-temperature heat bubble in the middle of a packed bed system and then use a two-step process wherein heat is (1) added to the bed via in-situ combustion, and then (2) removed from the bed via in-situ endothermic reforming. A key benefit of the invention is the ability to consistently manage and confine the high temperature bubble (e.g., $\geq 1500°$ C., preferably $\geq 1600°$ C., and sometimes even more preferably $\geq 1700°$ C.) in a reactor region(s) that can tolerate such conditions long term. The inventive apparatus and process provides for a substantially continuously operating, large-scale, cyclic, reverse-flow reactor system that is useful and operable on a commercial scale.

A reverse flow regenerative reactor is a reactor or reactor system, whereby materials flow therein for a period of time in one direction through all or selected portions of the reactor and react or are otherwise processed therein. The direction of flow is then reversed and other materials are fed from the opposite direction through the reactor to displace any remaining first materials or reaction products back in the direction opposite from the original flow. The introduced other materials also flow through the reactor for pyrolysis reaction therein. Thereby, the reactor bed or reactor media components are exposed to materials flowing in each direction through the reactor. Heat may be produced or added by the reactants flowing in one direction and that heat may be used to pyrolyze or otherwise facilitate product-generating reactions in the reactor. A substantial part of the heat is then removed during flow in the other direction. The pyrolysis reactor system includes one or more hot or heated reaction zones and a lower temperature quenching zone that serves to absorb heat from the reacted product to quench the reaction process. After cooling the reaction product, the heated quench zone is cooled by reversing the direction of flow through the reactor and feeding new supply of materials through the quench zone to absorb the quench zone heat and carry that heat back to the reaction zone where the recovered heat is conserved and reused to pre-heat the reaction zone and reactant materials. After reaction of the pre-heated reactants, the reactor is "regenerated" and ready to pyrolyze the hydrocarbonaceous reactant material (including any diluents or co-feeds) flowing through the reactor system in the opposite direction.

At least a portion of the feedstock that is transferred to or fed into the reactor system is, generally, (i) pyrolyzed (e.g., cracked) in the reaction zone to form the pyrolysis product (e.g., olefins, aromatics, and/or acetylene), and (ii) that cracked reaction product from (i) is quenched in the quenching zone to stop the reaction at the desired pyrolysis product step to thereby yield the pyrolysis product. If the reaction is not timely quenched and stopped, the reaction may continue decomposing the molecules into coke, elemental components, or other less desirable reaction product components.

Separated but simultaneous introduction of two or more reactants into the reactor system, such as through separate flow channels, can facilitate deferred reaction or combustion of the reactants until they are combined with each other, within the desired reactor zone to react with each other within that designated zone. Thereby, a heat bubble may be controllably and repeatedly positioned within the reactor system. In some embodiments, the reverse flow regenerative reactor may be described as comprising two zones/reactors: (1) a heat recuperating (first) zone/reactor, such as for quenching; and (2) a reforming (second) zone/reactor, such as for pyrolysis reaction and reforming. In some embodiments, however, the first and second reactors need not necessarily be separate components, but instead may be merely different sections of a common reactor. A reactant mixer may be provided intermediate the first and second reactors to assist with mixing and reacting of the separately introduced reactants. As a catalyst is preferably not required to facilitate reforming the hydrocarbon vapor to acetylene, in most preferred embodiments no catalyst is present in the reactor beds. However, there may be some applications that benefit from the presence of a catalyst within the reactor system to achieve a certain range of reforming performance and such embodiments are within the scope of the invention.

The requisite high temperature required for many pyrolysis reactions may be achieved by creating a high-temperature heat bubble in the middle of the reactor system or within one of the reactors of the reactor system, such as in packed or monolithic bed system. This heat bubble may be created via a two-step process wherein heat is (1) added to the reactor bed via delayed or deferred, in-situ combustion, and then (2) removed from the bed via in-situ endothermic reforming. A key benefit of the invention is the ability to consistently manage and confine the high temperature bubble (e.g., >1500° C.) in a reactor region(s) that comprise SRZ within and can tolerate such conditions long term. The inventive apparatus and process enable operation of a substantially continuously operating, large-scale, cyclic, commercial regenerative reactor system.

Figure 1B:
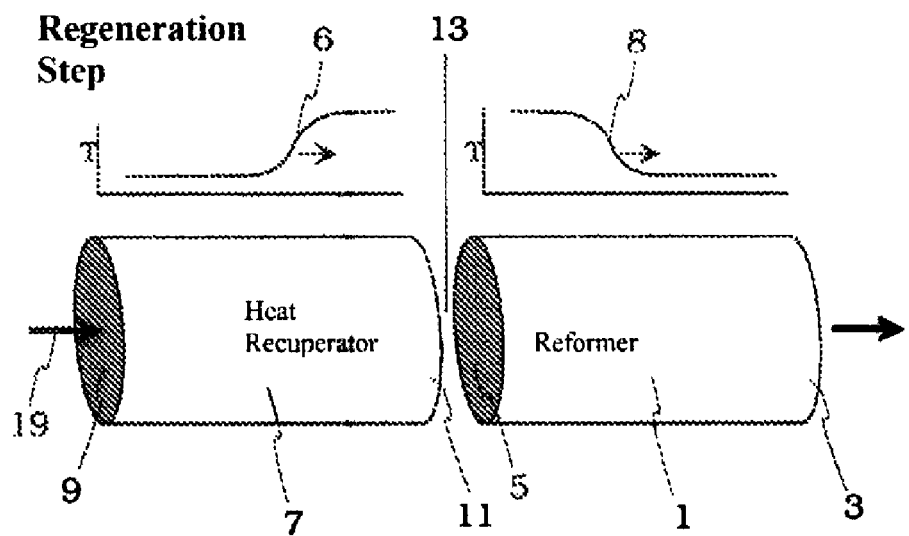

One generalized embodiment of a basic two-step asymmetric cycle regenerative reactor system according to the present invention is depicted in FIGS. 1a and 1b, illustrating a reactor system including two zones/reactors; a first or recuperator/quenching zone (7) and a second or reaction/reforming zone (1). Preferably, both the reaction zone (1) and the recuperator zone (7) comprise components fabricated from a SRZ material, preferably a PSRZ. The SRZ may be provided, for example, in one or more regenerative reactor beds that are useful for carrying out a high temperature chemical reaction. The SRZ may be used in construction of one or more embodiments, components, or regions of the reactor system, and may be of substantially any form or shape, such as but not limited to spheres, beads, honeycomb materials, tubes, extruded monoliths, bricks, tiles, and other molded or formed components that are exposed to the extreme temperatures. Additionally, if desired for some embodiments, the reactor system may also comprise other refractory materials in addition to the SRZ, in reactor regions that are not exposed to the most severe temperatures, such as glass or ceramic beads or spheres, metal beads or spheres, ceramics (including zirconia), ceramic or metal honeycomb materials, ceramic tubes, extruded monoliths, and the like, provided they are competent to maintain integrity, functionality, and withstand long term exposure to the relevant temperatures for that respective region of the reactor.

During the regeneration step, illustrated in FIG. 1(b), fuel and air may separately be channeled from a first end (19) of the first reactor (7) and then mixed as it exits the second end (11) or enters an optional mixing region (13), which may also include a mixer (not shown). The fuel and air mixture may cool the first reactor (7), producing a temperature gradient profile such as illustrated in graph (6). The mixed components preferably exothermically react (e.g., combust or burn) and the hot reaction product continues to pass into the second end (5) of the second reactor (1) and preferably through the second reactor (1) to exit the first end (3) of the second reactor. The hot reaction product may produce a temperature gradient through the second reactor (1), such as illustrated by graph (8). Then the process reverses (as illustrated in FIG. 1(a)) and one or more pyrolysis reaction feed materials (15) may be fed through the second reactor (1) to pyrolyze the feed, which is then cooled through the optional mixer and through the quenching, first reactor (7). Exemplary temperature profiles are illustrated in graphs (2) and (4).

Figure 2:
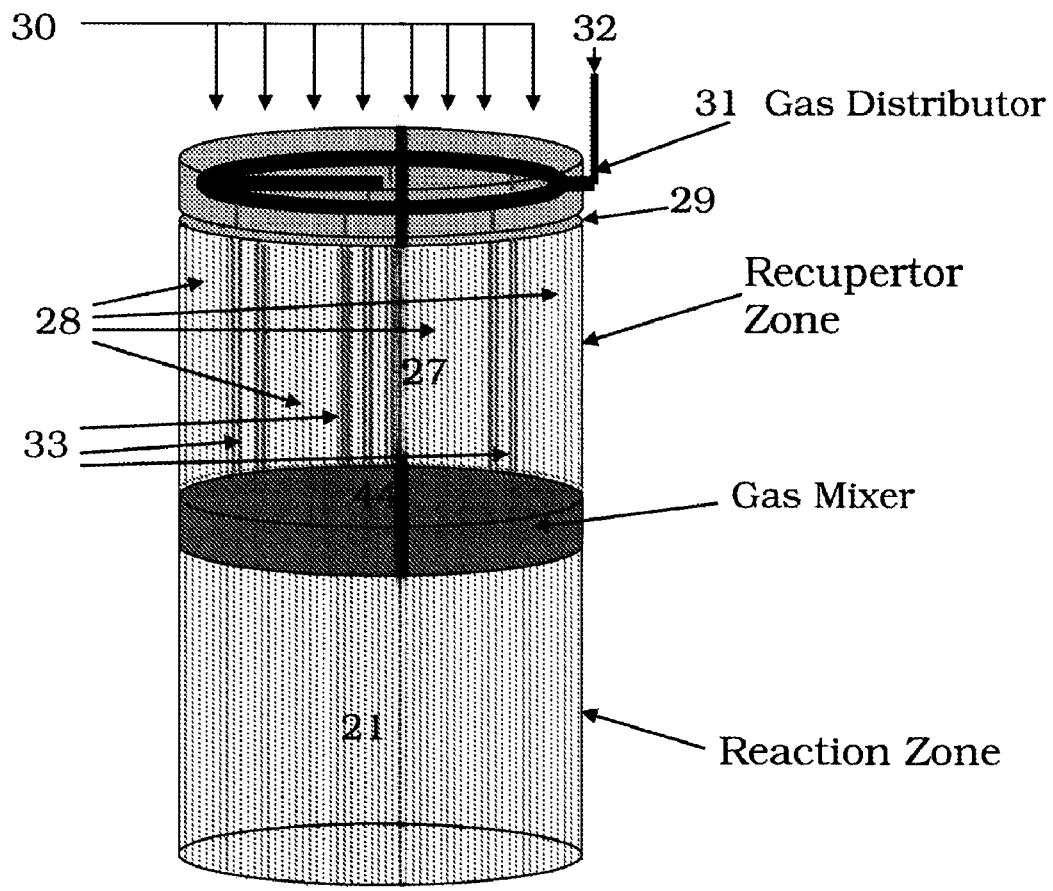
FIG. 2 is another simplified process flow diagram illustrating an embodiment of the invention.

FIG. 2 illustrates another simplified, exemplary, SRZ reactor system such as may be suitable in some applications for pyrolyzing hydrocarbon feed. The exemplary reactor is described in more detail in U.S. provisional patent application Ser. No. 60/933,044, filed Jun. 4, 2007, the entirety of which is incorporated herein. The reactor system of FIG. 2 is illustrative of any of a wide variety of more specific reactor designs that segregate the conveyance of each of two reactants from each other until the reactants reach a designated zone within the reactor system where they mix and react with each other. Such process and apparatus is particularly useful for deferring the exothermic reaction or combustion of reactants such as fuel and oxidant that provide the heat necessary to heat the pyrolysis zone. The inventive reactor system may utilize SRZ components in all regions of the reactor that may be subjected to the extreme temperatures, such as temperatures in excess of 1400° C. and even in excess of 1500° C. In some applications, the inventive SRZ may be useful, for example in applications having temperatures of in excess of 1700° C. and in some other applications the SRZ may be useful in the presence of temperatures in excess of 1800° C. FIG. 2 depicts a single reactor system, operating in the regeneration heat cycle. The reactor system preferably comprises two reactors zones or two reactor zones. The recuperator (27) is the zone primarily where quenching takes place and provides substantially isolated flow paths or channels (28) and (33) for transferring both of the quenching reaction gases (30) and (32) through the reactor media, without incurring combustion until the gasses arrive proximate or within the reactor core (44). FIG. 2 also illustrates one embodiment of a gas distributor (31) for dispersing one of the two reaction gases to desired locations about the end (29) of the reactor (27). The reformer (21) is the reactor where the majority of the regeneration heating and volatized hydrocarbon reformation or pyrolysis occurs. Although the first (27) and second reactors (21) in FIG. 2, or (7) and (1) respectively in FIGS. 1(a) and 1(b), in the illustrated reactor system are represented and identified as separately distinguishable reactors, it is understood and within the scope of the present invention that the first and second reactors may be manufactured, provided, or otherwise combined or integrated into a common single reactor bed, whereby the reactor system might be described as comprising merely a single reactor that integrates substantially the full extent of both cycles within the reactor.

The terms "first reactor" and "second reactor" are utilized for simplified explanation purposes and merely refer to the respective zones within the reactor system whereby each of the regeneration, reformation, quenching, etc., steps take place and do not require that separate reactors or components actually be utilized for the two reactors. However, most preferred embodiments will comprise a reactor system whereby the recuperator reactor includes conduits and channels as described herein, preferably formed from SRZ or more preferably PSRZ. The reformer reactor may similarly possess SRZ or preferably PSRZ. A SRZ or PSRZ mixer may be provided intermediate the first and second reactors to facilitate reactant mixing for good stoichiometric reaction and even heating. Other preferred embodiments may include a reformer reactor bed that is arranged different from the illustrated recuperator bed. In some embodiments, the reformer bed may comprise materials that are different from the materials that comprise the recuperator bed. However, SRZ or PSRZ is utilized in the extreme high temperature regions (e.g., >1500° C.). The bedding arrangement of the reformer or second reactor may be provided as desired or as prescribed by the application and no particular design is required herein of the reformer reactor, as to the performance of the inventive reactor system. Routine experimentation and knowledge of the volatized hydrocarbon pyrolysis art may be used to determine an effective reformer/second reactor design.

In a preferred embodiment of the present invention, a first reactant, such as a hydrocarbon fuel, is directed down one or more designated channels or conduits, while a second reactant, such as oxygen, is simultaneously directed down one or more other designated channels, through the reactor. During flow in the opposite direction, preferably both of the first and second sets of channels are simultaneously utilized to convey the pyrolyzed product through the reactor. Preferably the channels are fabricated from a SRZ, more preferably a PSRZ. In one preferred embodiment, the channels are included in one or more SRZ honeycomb monolith type structures. The term "honeycomb monoliths" is defined broadly to include but not be limited to extruded, ceramic structures as are generally known in the reaction industry, such as in catalytic converters, etc., capable of conveying a fluid through the framework of channels. The term "honeycomb" is also used broadly herein to refer to any framework of channels, regardless of cross-sectional geometry, that includes multiple substantially parallel flow paths or channels and is not intended to limit the structure or shape to any particular geometric shape. The channels each may have generally any cross-sectional shape, although a generally symmetrical cross-sectional shape may be preferred. Each monolith may include a single channel, a few channels, or multiple channels, e.g., tens, hundreds, or even thousands of channels, depending upon the size of the particular monoliths and reactors utilized therein. For example, in one embodiment, the conduits may have a diameter of only a few millimeters, and preferably on the order of about one millimeter. A reactor may comprise a single, a few, or even numerous monoliths. The monoliths may be further arranged into cells or groups of monoliths, wherein each or a group of cells is dedicated to conducting one of the two simultaneously conveyed materials, while another group of cells conveys the other material. A preferred monolith arrangement will provide low pressure loss or drop during reactant or product transference, while providing necessary product contact time and heat transfer during conductance. The arrangement preferably also provides adequate mixing of the conveyed materials after exiting the monoliths, such as in or near the reaction zone. In addition to providing a flow conduit, the channels also facilitate effective material isolation barriers (e.g., function such as conduit walls) to prevent cross flow or mixing between the first and second reactants and maintain a majority of the reactants effectively separated from each other until mixing is permitted. In some preferred embodiments of the present invention, the reactors are comprised of one or more extruded SRZ honeycomb monoliths, preferably PSRZ monoliths.

In some embodiments, the SRZ preferably provides a conduit packing with an average wetted surface area per unit volume that ranges from about 50 $ft^{-1}$ to about 3000 $ft^{-1}$, more preferably from about 100 $ft^{-1}$ to 2500 $ft^{-1}$, and still more preferably from about 200 $ft^{-1}$ to 2000 $ft^{-1}$, based upon the volume of the first reactor that is used to convey a reactant. Such wetted area values apply to the channels for both of the first and second reactants, with relatively thin walls separating the channels to facilitate good heat transfer between the reactants and the SRZ. The term "thin walls" refers to the distance through which heat must be moved within the solid portions of the SRZ component. Thus, for a bed of spherical packing would simply be the sphere diameter. For a reactor bed comprising honeycomb monolith structures, the relevant dimension is simply the wall thickness separating the flow channels. Preferred wall thickness of some honeycomb monoliths according to the present invention is less than 2.5 mm, more preferably less than 1.0 mm, down to a probable minimum wall thickness of not less than around 0.1 mm. These relatively thin walls are enabled by the strength and thermal shock resistance properties of the SRZ, as discussed previously. The durable, heat resistant SRZ material is ideal at enabling use of thin but strong reactor channel or wall components. The relatively high density also helps mitigate reactant cross-flow through the conduit or pore walls. The relatively high surface area per unit volume values facilitated by the high number of relatively small reactant pores or conduits are likely preferred for many embodiments to aid achieving a relatively quick change in the temperature through the reactor, such as generally illustrated by the relatively steep slopes in the exemplary temperature gradient profile graphs, such as in FIGS. 1(*a*), 1(*b*), and 6. The quick temperature change is preferred to permit relatively quick and consistent quenching of the reaction to prevent the reaction from continuing and creating coke. The relatively high thermal stability, high thermal shock resistance, and high heat transfer capability of SRZ also enables these desired quick temperature changes, without experiencing material failure due to thermal shock degradation. The prescribed SRZ is highly resistant to such degradation.

In some embodiments, a preferred SRZ reactor will provide media channels and other high temperature-exposed components and packing that includes a high volumetric heat transfer coefficient (e.g., greater than or equal to 0.02 cal/$cm^3 s°$ C., preferably greater than about 0.05 cal/$cm^3 s°$ C., and most preferably greater than 0.10 cal/$cm^3 s°$ C.), with corresponding low resistance to flow (low pressure drop), have operating temperature range consistent with the highest temperatures encountered during regeneration, have high resistance to thermal shock, and have high bulk heat capacity (e.g., at least about 0.10 cal/$cm^{3°}$ C., and preferably greater than about 0.20 cal/$cm^{3°}$ C.). As with the high surface area values, these relatively high volumetric heat transfer coefficient values, high strength (MOR), and other properties provided by SRZ are also likely preferred for many embodiments to aid in achieving a relatively quick change in the temperature through the reactor, such as generally illustrated by the relatively steep slopes in the exemplary temperature gradient profile graphs, such as in FIGS. 1(*a*), 1(*b*), and 6. The quick temperature change permits relatively quick and consistent quenching of the reaction to prevent the reaction from continuing too long and creating coke or carbon buildup. The cited values are projected averages based upon the prospective volume of a typical reactor used for conveyance of a reactant.

Alternative embodiments may use SRZ reactor media other than the described and preferred honeycomb monoliths, such as whereby the channel conduits/flow paths are substantially linear and tubular. Other alternative embodiments may include a more tortuous pathways (e.g. convoluted, complex, winding and/or twisted but not linear or tubular) through a SRZ component, than the previously described monoliths, including but not limited to labyrinthine, variegated flow paths, conduits, tubes, slots, and/or a pore structure having channels through a portion(s) of the reactor and may include barrier portion, such as along an outer surface of a segment or within sub-segments, having substantially no effective permeability to gases, and/or other means suitable for preventing cross flow between the reactant gases and maintaining the first and second reactant gases substantially separated from each other while axially transiting the recuperator (27). For such embodiments, the complex flow path may create a lengthened effective flow path, increased surface area, and improved heat transfer. Such design may be preferred for reactor embodiments having a relatively short axial length through the reactor. Axially longer reactor lengths may experience increased pressure drops through the reactor. However for such embodiments, the porous and/or permeable media may include, for example, at least one of a packed bed, an arrangement of tiles, a permeable solid media, a substantially honeycomb-type structure, a fibrous arrangement, and a mesh-type lattice structure. It may often be preferred that the SRZ matrix provides high surface area to facilitate good heat exchange with the reactant and produced gases.

Typical conditions may include a residence time from 0.001 to 1.0 seconds and may typically include, for example, a pressure from about 5 to 50 psia (34 to 345 kPa). In some embodiments, the reactor conditions may be at a vacuum pressure, such as less than 15 psia (103 kPa). For purposes of this discussion, the term "residency time" refers to the time exposed to temperatures typically in excess of about 1200° C. For example, in many useful reactors, the residency time at such temperature, and more preferably at temperatures in excess of 1500° C., is preferably less than about 0.005 seconds, such as within a range of from 0.001 to 0.010 seconds, but more preferably within a range of from 0.001 to about 0.005 seconds. However, the total time in the reactor bed system could be longer, such as on order of 0.030 seconds or greater, depending upon the quenching process and reactor channel length. Cracked pyrolysis product may be removed from the reactor system, such as via lines 49 and/or 51 and transferred to other processes for recovery of the various component products of the cracked product. The reactor system may also include additional feed lines (not shown) such as fuel and oxidant feed, stripping agent feed, exhaust lines, etc.

The regenerative pyrolysis reactor system may heat the hydrocarbon feedstock to temperatures in excess of 1200° C., preferably in excess of 1500° C., more preferably in excess of 1700° C. In some reactions, it may even be preferable to heat the feeds for very short time duration, such as less than 0.1 seconds, to a temperature in excess of 1800° C. or even in some instances in excess of 2000° C. An exemplary preferred process may pyrolyze the feed stream within the reactor, such as at temperatures of from about 1500° C. to about 1900° C., and more preferably from about 1600° C. to about 1700° C. Exemplary residency times preferably may be short, such as less than 0.1 seconds and preferably less than about 5 milliseconds. In some aspects, the conversion or cracking of the separated vapor phase may be performed in the presence of hydrogen, hydride, other hydrocarbons, and/or other diluents or stripping agents. The conversion of the vapor fraction into higher value hydrocarbons such as acetylene typically requires a high reformation temperature, which in the past has been a significant barrier to commercialization and efficiency.

In one preferred embodiment, the reactor pores or channels comprise PSRZ materials that provide the necessary heat transfer capacity to create the temperature profiles (4) and (8) illustrated in FIG. 1, at the space velocity conditions of operation. Adequate heat transfer rate is characterized by a heat transfer parameter $\Delta T_{HT}$, below about 500° C., more preferably below about 100° C., and most preferably below about 50° C. The parameter $\Delta T_{HT}$, as used herein, is the ratio of the bed-average volumetric heat transfer rate that is needed for recuperation, to the volumetric heat transfer coefficient of the bed, $h_v$. The volumetric heat transfer rate (e.g. cal/$cm^3$ sec) that is sufficient for recuperation is calculated as the product of the gas flow rate (e.g. gm/sec) with the gas heat capacity (e.g. cal/gm ° C.) and desired end-to-end temperature change (excluding any reaction, e.g. ° C.), and then this quantity divided by the volume (e.g. $cm^3$) of the recuperator zone (27) traversed by the gas. The $\Delta T_{HT}$ in channel (28) is computed using gas (30), channel (33) with gas (32), and total recuperator zone (27) with total gas. The volumetric heat transfer coefficient of the bed, $h_v$, is typically calculated as the product of a area-based coefficient (e.g. cal/$cm^2 s°$ C.) and a specific surface area for heat transfer ($a_v$, e.g. $cm^2/cm^3$), often referred to as the wetted area of the packing.

Typical conditions may include a residence time of from 0.001 to 1.0 seconds and may typically include, for example, a pressure from about 5 to 50 psia (34 to 345 kPa). In some embodiments, the reactor conditions may be near atmospheric pressure, such as from about 13 to about 25 psia (90 to 172 kPa), and in other embodiments at a vacuum pressure, such as less than 15 psia (103 kPa). Cracked pyrolysis product may be removed from the reactor system and transferred to other processes for recovery of the various component products of the cracked product. In addition to the hydrocarbon feed to be cracked, the reactor system may also include additional feeds, such as fuel, oxidant, steam, hydrogen, or other hydrocarbon co-reactants, or other co-feeds. In some aspects, the conversion or cracking of the hydrocarbon feed may be performed in the presence of hydrogen, hydrides, other hydrocarbons, and/or other diluents or stripping agents.

The conversion of the vapor fraction into higher value hydrocarbons such as acetylene typically requires a high reformation temperature, which in the past has been the most significant barrier to commercialization and efficiency. The regenerative PSRZ pyrolysis reactor system may heat the hydrocarbon feedstock to temperatures in excess of 1200° C., preferably in excess of 1500° C., more preferably in excess of 1600° C., and sometimes more preferably in excess of 1700° C. In some reactions, it may even be preferable to heat the feeds for very short time duration to a temperature of even up to or in excess of 2000° C. An exemplary preferred process may pyrolyze the feed stream within the PSRZ reactor, such as at temperatures of from about 1500° C. to about 2000° C., and more preferably from about 1500° C. to about 1900° C., and still more preferably from about 1600° C. to about 1700° C. Exemplary residency times preferably may be short, such as less than 0.1 seconds and preferably less than about 5 milliseconds.

Preferably, the SRZ includes a thermal shock resistance rating (determined as discussed above, related to ASTM 1525-04) that demonstrates a total crack length per unit area after quickly quenching a test specimen of the SRZ at 1100° C. into a water bath at room temperature, is not greater than 30 cm/cm$^2$. To put this in perspective, this may typically represent a thermal shock resistance rating that is at least 3 times better than the thermal shock resistance rating of a common standard engineering grade alumina (>=80% $Al_2O_3$). In a more preferred embodiment, the SRZ is a PSRZ that includes a thermal shock resistance rating that demonstrates a total crack length per unit area after quenching a test specimen of the SRZ at 1100° C. into a water bath at room temperature, is not greater than 5 cm/cm$^2$. To put this in perspective, this may typically represent a thermal shock resistance rating that is at least 4 times better than the thermal shock resistance rating of a common standard engineering grade alumina.

It is also preferred that the SRZ comprises a modulus of rupture (MOR) mechanical flexural strength of not less than 2 kpsi (13.8 MPa) prior to firing the SRZ-laden reactor or otherwise initially heating the SRZ material to a temperature of at least 1000° C. More preferably, it is preferred that the SRZ comprises a MOR mechanical flexural strength of not less than 2 kpsi (13.8 MPa) when the reactor is fired or otherwise heated to a temperature in a range of from 1000° C. to 1800° C. Still more preferably, it may be preferred that the SRZ comprises a MOR mechanical flexural strength of not less than 2 kpsi (13.9 MPa) when the reactor is fired or otherwise heated to a temperature in a range of from 1000° C. to 2000° C.

Many preferred apparatus according to the present invention may also include an SRZ that comprises an MOR mechanical flexural strength measured at 50° C. after water bath quenching from a temperature in a range of from 1000° C. to 1800° C. that is at least 70% of said stabilized refractory grade zirconia's MOR flexural strength measured at a temperature in a range of from 1000° C. to 1800° C. (The procedure used is as described in ASTM C 1525-4.) Thereby, the preferred PSRZ material does not lose more than 30% of its MOR at reactor operating temperature as compared to its MOR strength at ambient temperature. Still more preferred embodiment may include an SRZ that comprises an MOR mechanical flexural strength measured at 50° C. after waterbath quenching from a temperature in a range of from 1000° C. to 1800° C. that is at least 75%, and even more preferably, at least 80%, of said stabilized refractory grade zirconia's MOR flexural strength measured at a temperature in a range of from 1000° C. to 1800° C. Thereby, the preferred PSRZ material does not lose more than 25%, and even more preferably not more than 20%, respectively, of its MOR at reactor operating temperature as compared to its MOR strength at ambient temperature.

In preferred embodiments, the SRZ is stabilized by at least one stabilization component that includes at least one of CaO, MgO, $Y_2O_3$, $CeO_2$, and mixtures thereof. Preferably, the SRZ comprises at least one weight percent (1.0 wt. %) of such stabilization component, based upon the total weight of the stabilized zirconia. In still other embodiments, the SRZ may further comprise one or more secondary stabilization component, including but not limited to secondary oxides selected from the group consisting of Al, Si, Mg, Ca, Y Fe, Mn, Ni, Co, Cr, Ti, Hf, V, Nb, Ta, Mo, W, Sc, La, and Ce, and mixtures thereof. Preferably, the weight of secondary oxides in the SRZ ranges from about 0.001 percent to about 10 percent by weight, based upon the weight of the stabilized zirconia. In some reactor systems, the pyrolysis reactor may comprise another refractory material, such as a ceramic or other refractory material, in a portion of the reactor system that is exposed to temperatures that are lower than the portion of the reactor system that comprises the SRZ. Such arrangement may reduce the cost of the reactor system as compared to a reactor system wholly comprising SRZ.

In another aspect, this invention also includes a reverse flow regenerative pyrolysis reactor system comprising: a first reactor and a second reactor in flow communication with the first reactor, the first reactor comprising a first channel for conveying a first reactant through the first reactor to the second reactor and a second channel for conveying a second reactant through the first reactor to the second reactor, the first reactant exothermically reacting with the second reactant in the second reactor; wherein the second reactor comprises a SRZ.

In some two-reactor embodiments of a reactor system, only one of the reactors, such as the first reactor or the second reactor, may comprise SRZ, while the other reactor is comprised of other refractory materials. However, in most preferred embodiments, each of the first and second reactors will comprise at least some SRZ, if not comprised wholly of SRZ. Preferably, each of the various segregated channels within a reactor or reactor system, such as the first channel and the second channels, comprise SRZ, more preferably PSRZ. Thereby each of the first reactant and second reactant are conducted through a channel comprised of SRZ. Many reactor embodiments may also include a mixer comprised of SRZ, preferably PSRZ, positioned between the first and second reactors, to combine at least a portion of the first reactant with at least a portion of the second reactant.

In still another aspect, the invention includes a method for pyrolyzing a hydrocarbon feedstock using a reverse flow regenerative pyrolysis reactor comprising the steps of: providing a reverse flow regenerative pyrolysis reactor including a SRZ, preferably a PSRZ, in a heated reaction zone of the reactor; and pyrolyzing a hydrocarbon feedstock within the heated reaction zone. The pyrolysis reaction zone, whether located within one or both reactors of a two-reactor system or within the reaction zone of a single-reactor reactor system, is preferably heated by deferred combustion. The various process steps and preferred apparatus associated with such method are discussed in more detail previously throughout this disclosure.

While the present invention has been described and illustrated with respect to certain embodiments, it is to be understood that the invention is not limited to the particulars disclosed and extends to all equivalents within the scope of the claims.

What is claimed is:

1. A reverse flow regenerative pyrolysis reactor system comprising:
    a first reactor and a second reactor in flow communication with said first reactor, said first reactor comprising a first channel for conveying a first reactant through the first reactor to said second reactor and a second channel for conveying a second reactant through the first reactor to said second reactor, wherein said second reactor is configured to exothermically react the first reactant with the second reactant in the second reactor to heat the second reactor and endothermically react a hydrocarbon feedstock once exothermic reaction products are removed, wherein said second reactor comprises a stabilized refractory grade zirconia in a reactive region of said second reactor, and wherein said stabilized refractory grade zirconia is stabilized by at least one stabilization component comprising at least one of CaO, MgO, $Y_2O_3$ $CeO_2$, and mixtures thereof and comprises at least 1.0 weight percent of said stabilization component, based upon the total weight of said stabilized refractory grade zirconia.

2. The system of claim 1, further comprising insulation material in a substantially non-reactive region of at least one of said first reactor and second reactor.

3. The system of claim 1, wherein said reactive region comprises a honeycomb monolith having flow channels within said monolith for conducting at least one of a pyrolysis reactant and a pyrolysis product through said monolith.

4. The system of claim 1, wherein said stabilized refractory grade zirconia comprises a thermal shock resistance rating that demonstrates a total crack length per unit area after quenching said stabilized refractory grade zirconia from 1100° C. into a water bath to a temperature of 50° C. is not greater than 30 cm/cm$^2$.

5. The system of claim 1, wherein said stabilized refractory grade zirconia comprises a modulus of rupture mechanical flexural strength of not less than 13.8 MPa prior to initially heating the stabilized refractory grade zirconia to 1000° C.

6. The system of claim 1, wherein said stabilized refractory grade zirconia comprises a modulus of rupture mechanical flexural strength of not less than 13.8 MPa when heated to a temperature in a range of from 1000° C. to 1800° C.

7. The system of claim 1, wherein said stabilized refractory grade zirconia comprises a modulus of rupture mechanical flexural strength of not less than 13.8 MPa at a temperature in a range of from 1000° C. to 2000° C.

8. The system of claim 1, wherein said stabilized refractory grade zirconia comprises a modulus of rupture mechanical flexural strength measured at 50° C. after quenching from a temperature in a range of from 1000° C. to 1800° C. that is at least 70% of said stabilized refractory grade zirconia's modulus of rupture mechanical flexural strength measured at a temperature in a range of from 1000° C. to 1800° C.

9. The system of claim 1, wherein said stabilized refractory grade zirconia comprises a modulus of rupture mechanical flexural strength measured at 50° C. after quenching from a temperature in a range of from 1000° C. to 1800° C. that is at least 80% of said stabilized refractory grade zirconia's modulus of rupture mechanical flexural strength measured at a temperature in a range of from 1000° C. to 1800° C.

10. The system of claim 1, wherein said stabilized refractory grade zirconia further comprises from 0.001 percent to 10 percent by weight, based upon the weight of the stabilized refractory grade zirconia, of secondary oxides that comprise elements selected from the group consisting of Al, Si, Mg, Ca, Y Fe, Mn, Ni, Co, Cr, Ti, Hf, V, Nb, Ta, Mo, W, Sc, La, and Ce, and mixtures thereof.

11. The system of claim 10, wherein said partially stabilized refractory grade zirconia is stabilized by at least one stabilization component comprising at least one of CaO, MgO, $Y_2O_3$, $CeO_2$, and mixtures thereof.

12. The system of claim 1, wherein said reactive region of at least one of said first reactor and second reactor includes at least one of a honeycomb monolith, a reactor bed, a reactor conduit, and a reactant mixer.

13. The system of claim 1, wherein said regenerative pyrolysis reactor comprises a deferred combustion reactor.

14. The system of claim 1, wherein said stabilized refractory grade zirconia includes a partially stabilized refractory grade zirconia.

15. The system of claim 14, wherein said partially stabilized refractory grade zirconia comprises a monolith having flow channels within said monolith for conducting at least one of a pyrolysis reactant and a pyrolysis product through said monolith.

16. The system of claim 14, wherein said partially stabilized refractory grade zirconia comprises a thermal shock resistance rating that demonstrates a total crack length per unit area after quenching said partially stabilized refractory grade zirconia from 1100° C. into a water bath to a temperature of 50° C. is not greater than 5 cm/cm$^2$.

17. The system of claim 14, wherein said partially stabilized refractory grade zirconia comprises a modulus of rupture mechanical flexural strength of not less than 27.6 MPa when heated to a temperature in a range of from 1000° C. to 1800° C.

18. The system of claim 14, wherein said partially stabilized refractory grade zirconia comprises a modulus of rupture mechanical flexural strength measured at 50° C. after quenching from a temperature in a range of from 1000° C. to 1800° C. that is at least 80% of said partially stabilized refractory grade zirconia's modulus of rupture mechanical flexural strength measured at a temperature in a range of from 1000° C. to 1800° C.

19. The system of claim 1, wherein said second reactor comprises said stabilized refractory grade zirconia.

20. The system of claim 19, wherein said first reactor comprises said stabilized refractory grade zirconia.

21. The system of claim 1, further comprising a reactant mixer positioned intermediate said first reactor and said second reactor to combine at least a portion of said first reactant with at least a portion of said second reactant, said reactant mixer comprising stabilized refractory grade zirconia.

22. A method for pyrolyzing a hydrocarbon feedstock using a reverse flow regenerative pyrolysis reactor system comprising the steps of:
    providing a reverse flow regenerative pyrolysis reactor system comprising a first reactor and a second reactor in flow communication with the first reactor including a stabilized refractory grade zirconia in a reactive region of at least one of said first reactor and said second reactor;
    exothermically reacting a fuel and oxidant within said reactive region to heat said reactive region with combustion products, wherein said fuel is conveyed through a first channel in a first reactor and said oxidant is conveyed through a second channel in said first reactor;

removing the combustion products; and pyrolyzing a hydrocarbon feedstock within said reactive region.

23. The method of claim 22, further comprising the step of heating said reactive region by deferred combustion.

24. The method of claim 22, wherein the pyrolyzing the hydrocarbon feedstock is at temperatures from about 1500° C. to about 1900° C.

25. The method of claim 22, wherein the pyrolyzing the hydrocarbon feedstock is at temperatures from about 1600° C. to about 1700° C.

* * * * *